United States Patent [19]

Akimova et al.

[11] 4,407,793

[45] Oct. 4, 1983

[54] COMPOSITION FOR TEMPORARY SUBSTITUTION OF BONE TISSUE DEFECTS

[76] Inventors: Alla Y. Akimova, ulitsa Kosmonavta Volkova, 7, kv. 15; Anatoly B. Davydov, ulitsa Krasny Kazanets, 19, kv. 283; Galina M. Derkach, proezd Shokalskogo, 2-a, kv. 81; Valeria I. Timokhina, Yaroslavskoe shosse, 4, korpus 4, kv. 373, all of Moscow; Sergei S. Tkachenko, Svetlanovsky prospekt, 35, kv. 16; Vladimir V. Rutsky, ulitsa Kosinova, 7, kv. 10, both of Leningrad; Mstislav V. Volkov, ulitsa Stroitelei, 6, korpus 1, kv. 63, Moscow; Irina S. Shepeleva, Bulvar generala Karbysheva, 4, kv. 15, Moscow; Alexandr V. Shiryaev, Zatsepsky val, 5, kv. 80, Moscow; Semen I. Lipkin, Leningradskoe shosse, 128, kv. 150, Moscow; Vladimir M. Musyanovich, ulitsa 700-letia Lvova, 53, kv. 84, Lvov, all of U.S.S.R.

[21] Appl. No.: 382,321

[22] Filed: May 26, 1982

[51] Int. Cl.$^3$ .............................................. A61K 31/78
[52] U.S. Cl. ..................................... 424/81; 424/154; 424/156
[58] Field of Search .......................... 424/81, 154, 156

[56] References Cited

U.S. PATENT DOCUMENTS 4,093,576  6/1978  de Wijn ................................. 424/81
4,192,021  3/1980  Deibig et al. ....................... 106/161
4,239,113 12/1980  Gross et al. .......................... 424/81

OTHER PUBLICATIONS

Draenert–Chem. Abst. vol. 94 (1981) p. 96385j.

*Primary Examiner*—Sam Rosen
*Attorney, Agent, or Firm*—Ladas & Parry

[57] ABSTRACT

The composition for a temporary substitution of bone tissue defects according to the present invention consists of α-cyanacrylic acid esters and a powder-like filler which is a calcium salt of an organic or inorganic acid with a particle size of from 0.01 to 0.5 mm, the components being used in the following proportions, percent by weight:

| | |
|---|---|
| α-cyanacrylic acid esters | 60 to 40 |
| calcium salt of organic or inorganic acid with a particle size of 0.01 to 0.5 mm | 40 to 60. |

The composition of the present invention is useful for fixation of bone fragments, fixation of bone homotransplantant in the case of anterior cervical spondyolodosis, temporary filling of bone cavities and the like.

7 Claims, No Drawings

COMPOSITION FOR TEMPORARY SUBSTITUTION OF BONE TISSUE DEFECTS

FIELD OF THE INVENTION

The present invention relates to medicine and, more specifically, to a composition for a temporary substitution of bone tissue defects. The composition is useful both individually or in combination with an ultrasonic treatment for the fixation of bone fragments, fixation of bone homotransplantant at anterior cervical spondylosis, tenporary filling of bone cavities, recovery of articular surfaces, fixation of on-bone implanted active electrodes for a subsequent electrostimulation of osteogenesis and the like.

BACKGROUND OF THE INVENTION

Known in the art are compositions for a temporary substitution of defects of bone tissue which are based on α-cyanacrylates and fillers, e.g. a composition comprising ethyl-α-cyanacrylate and bone chips. (In coll. "Osteosynthesis, Bone Welding and Cutting of Live Biological Tissues by Ultrasonic Wave Guides", Moscow, 1970, p. 12–15, "Orthopedics, Traumatology and Prosthetics", Moscow, 1975, No. 10, p. 18–23).

In practical use of this prior art composition bone chips are placed onto a bone substrate remaining after resection, added with ethyl-α-cyanacrylate and under the effect of ultrasonic treatment the composition is transformed into a solid conglomerate temporarily substituting the bone defect. The composition comprises 50% by weight of bone chips and 50% by weight of ethyl-α-cyan-acrylate. Bone chips comprise an active component relative to ethyl-α-cyanacrylate and causes an instant curing of the latter. This does not enable a precise metering of amounts of the components, formation of a homogeneous composition which, in turn, results in instable durability characteristics.

Furthermore, bone chips get rapidly impregnated with ethyl-α-cyanacrylates which results in the formation of a monolithic conglomerate hindering regeneration of bone tissue.

Also known in the art is a composition containing 70–50% by weight and 30–50% by weight of bone chips with its particles coated with an envelope of a non-toxic, water-soluble and insoluble in ethyl-α-cyanacrylate polymer-dextrane (cf. Vedenkov V. G., Akimova A. Ya., Bukhtiarova G. Ya., Derkach G. M., Cys' I. N. "Development of a composition for ultrasonic welding and melting-on of bone tissues based on modified bone shavings and ethyl-α-cyanacrylate". Ultra sound and other kinds of energy in surgery. Moscow, 1974, p. 62–66).

Coating of particles of bone chips with an envelope of a polymer soluble in water and insoluble in ethyl-α-cyanacrylate has made it possible to ensure a more precise dosage of the components, reduce monolithic character of the forming conglomerate.

However, the use of bone chips in the composition does not make it possible to obtain a uniform blend after mixing of the components. For this reason in the cured conglomerate there can be formed zones with an increased content of bone chips and zones consisting essentially of polyethyl-α-cyanacrylate. The distribution of the components in the cured conglomerate affects the speed of its destruction under the effect of the organism media which, in turn, can slow-down the speed of regeneration of bone tissue. Therefore, in the use of modified bone chips as a filler it is impossible to obtain stable reproducible results as regards the speed of biodestruction of the conglomerate.

The disadvantage of the above-mentioned composition also resides in that bone chips comprise an expensive product not suitable for standardization. Furthermore, the use of ethyl-α-cyanacrylate in this composition results in the formation of a conglomerate resistant to the effect of the organism media and its biodestruction proceeds but slowly, wherefore the conglomerate hinders regeneration of the newly formed bone tissue. In view of the above-listed disadvantages this composition has not found any suitable application in practical medicine.

SUMMARY OF THE INVENTION

It is an object of the present invention to provide a composition for a temporary substitution of bone tissue defects which would be useful in medical practice and enabling reduced time of biodestruction of the cured conglomerate, thus providing favourable conditions for regeneration of bone tissue and reducing the time of treatment and rehabilitation of patients.

This object is accomplished by that the composition for a temporary substitution of bone tissue defects on the basis of α-cyanacrylic acid esters and a filler, according to the present invention, contains a powder-like filler—a salt of calcium of an organic or inorganic acid with a particle size of from 0.01 to 0.5 mm, the components being present in the following proportions, percent by weight:

| | |
|---|---|
| α-cyanacrylic acid esters | 60 to 40 |
| calcium salt of organic or inorganic acid with a particle size of 0.01 to 0.5 mm | 40 to 60. |

As calcium salts of organic or inorganic acids the composition according to the present invention can incorporate calcium carbonate, calcium gluconate, calcium chloride, calcium phosphate, calcium citrate. It is preferable that the composition would contain calcium gluconate or calcium carbonate. To impart a predetermined physiological effect to the preparation, it should be added with regeneration stimulants and antiseptics.

The preparation according to the present invention preferably contains, as a regeneration stimulant, 4-uracylcarboxylic acid (orotic acid) or its derivatives in an amount of from 10 to 30% by weight.

As the antiseptic the composition according to the present invention preferably incorporates 1,4-di-N-oxy 2,3-dihydroxy-methylquinoxaline or 1,4-di-N-oxy 2,3-diacetoxymethylquinoxaline in an amount of from 10 to 30% by weight.

As the composition base intended for the provision of adjusted time limits of biodestruction of the cured conglomerate, it is preferred to use a mixture of ethyl-α-cyanacrylate and ethoxyethyl-α-cyanacrylate, the components being present in the following proportions, percent by weight:

| | |
|---|---|
| ethyl-α-cyanacrylate | 80 to 95 |
| ethoxyethyl-α-cyanacrylate | 20 to 5. |

DETAILED DESCRIPTION OF THE INVENTION

The composition is prepared directly before use by mixing the composition components at room temperature in a polyethylene or fluoroplastic vessel. After mixing of the components a paste-like mass is formed which has adherence to the bone tissue. The life time of the composition ranges within 5 to 30 minutes depending on the employed calcium salt and proportions of the components.

The paste-like mass is applied onto a preliminarily dried surface of the bone tissue. To accelerate the process of curing of the composition use can be made of an ultrasonic treatment (amplitude 50–55 μm, frequency 26.5 kHz, treatment time 30–60 seconds).

Curing of the composition by the effect of ultra sound occurs within 1–2 seconds, without ultrasonic treatment-within 5 to 30 minutes. The use of calcium salt in the composition according to the present invention as a filler makes it possible to produce a uniform mixture after blending of the components which, in turn, ensures reproducible data as regards the speed of biodestruction of the cured conglomerate.

The use of the composition containing a calcium salt and a mixture of ethyl- and ethoxyethyl-α-cyanacrylate makes it possible to reduce the duration of biodestruction of the cured conglomerate by 0.8–2 times as compared with the composition incorporating bone chips and ethyl-α-cyanacrylate.

To increase hydrophilic power of the composition, particles of the salt of calcium can be coated with envelopes of a non-toxic polymer soluble in water and insoluble in α-cyanacrylates.

As the salts of calcium use can be made of different organic and inorganic calcium salts such as calcium carbonate, calcium chloride, calcium phosphate, calcium citrate, calcium gluconate and the like.

As the regeneration stimulants use is made of 4-uracylcarboxylic acid, potassium salt of 4-uracylcarboxylic acid and the like. As antiseptics use can be made of antibiotics or such compounds as 1,4-di-N-oxide 2,3-dihydroxymethylquinoxaline, 1,4-di-N-oxy 2,3-diacetoxymethylquinoxaline. The regeneration stimulants and antiseptics are introduced in an amount ranging from 10 to 30% by weight.

The composition according to the present invention has no toxic effect, ensures a lasting evolution of the regeneration stimulants into the trauma zone, retains bactericidal properties within 2–3 weeks after the operation and provides no hindering effect on regeneration of the bone tissue.

The composition for a temporary substitution of bone tissue defects has been tested in clinics on 200 patients. The composition is prepared right before use and applied onto preliminarily dried surface of a bone tissue. The composition has thus been tested.

For filling of bone cavities in radical operations on patients suffering from chronical osteomyelitis including shoulder osteomyelitis, femoral osteomyelitis, tibial osteomyelitis, ishiatic osteomyelitis. In all cases there is observed healing of wounds by primary extension; no complications associated with the use of the composition according to the present invention are observed.

The use of the composition according to the present invention makes it possible to avoid drainage.

In reconstruction operations of wrongly consolidated fractures, rheumatic polyarthritis, for fixation of bone fragments of forearm, peroneal bone, shinbone, collar bone, fixation of bone transplantants with the use of the composition of this invention healing occured without complications. In none of the cases any secondary displacement was observed.

In fixation of bone grafts to prevent micro- and macro-shiftings in reconstruction steps of osteoplastic operations of chronical otitis media, non-purulent disease of middle ear, chronical diseases of nasal accessory sinuses, maxillary sinus cyst, ethmoidal sinus osteoma with the use of the composition according to the present invention no complications were observed. The use of the composition made it possible to reduce the duration of stay of the patients in the hospital by 4–6 days, as well as to ensure a strict restoration of anatomic reliefs which is especially important from both functional and cosmetic standpoint. The composition according to the present invention has been also tested for fixation of on-bone implanted electrodes for carrying out electrostimulation, as well as for fixation of bone homotransplantant at anterior cervical spondyoledosis.

The use of the composition according to the present invention has made it possible to avoid an external fixation of the cervical part of spinal column thus allowing an early activization of patients. The duration of stay of the patients in hospital was reduced by 2 weeks. No shiftings and complications due to the use of the composition were observed.

For a better understanding of the present invention some specific examples illustrating the composition for a temporary substitution of defects of bone tissue are given hereinbelow.

EXAMPLE 1

A composition for a temporary substitution of bone tissue defects consists of the following components, percent by weight:

| | |
|---|---|
| calcium carbonate with a particle size of from 0.01 to 0.05 mm | 50 |
| ethyl-α-cyanacrylate | 45 |
| ethoxyethyl-α-cyanacrylate | 5 |

A sterile weighed portion encapsulated in dextrane, mixed with α-cyanacrylic acid esters till the formation of a paste-like mass. The cohesion strength of the cured conglomerate determined on the instrument Dinstat Dis (ultimate bending strength) is 200 to 250 kg/cm$^2$. The sample weight decrease after the residence in water at the temperature of 37° C. for 28 days is 8%. The composition is intended for fixation of bone fragments, bone transplantant, securing of on-bone implanted active electrodes.

EXAMPLE 2

A composition for a temporary substitution of bone tissue defects consists of the following components, percent by weight:

| | |
|---|---|
| calcium gluconate with a particle size of from 0.05 to 0.2 mm | 60 |
| ethyl-α-cyanacrylate | 32 |
| ethoxyethyl-α-cyanacrylate | 8. |

A sterile weighed portion of calcium gluconate is mixed with α-cyanacrylic acid esters to obtain a paste-like mass. The cohesion strength of the cured conglomerate determined on the instrument Dinstat Dis (ultimate bending strength is 230–250 kg/cm². The sample weight decrease after residence in water at the temperature of 37° C. for 28 days is 20%. The composition is intended for fixation of bone fragments, bone transplantants, securing of on-bone implanted active electrodes, restoration of articular surfaces.

EXAMPLE 3

A composition for a temporary substitution of bone tissue defects consists of the following components, percent by weight:

| | |
|---|---|
| disubstituted calcium orthophosphate | 60 |
| ethyl-α-cyanacrylate | 40. |

The composition is prepared following the procedure similar to that described in Example 1 hereinbefore. The cohesion strength as determined on the instrument Dinstat Dis (ultimate bending strength) is 250–280 kg/cm². The sample weight decrease after residence in water at the temperature of 37° C. for 28 days is 5%. The composition is intended for fixation of on-bone implanted active electrodes, restoration of articular surfaces.

EXAMPLE 4

A composition for a temporary substitution of bone tissue defects consists of the following components, percent by weight:

| | |
|---|---|
| calcium gluconate | 20 |
| potassium salt of 4-uracylcarboxylic acid | 20 |
| ethyl-α-cyanacrylate | 40 |
| ethoxyethyl-α-cyanacrylate | 10. |

The composition is prepared in a manner similar to that described in Examples 1 and 2. The conhesion strength of the cured conglomerate determined on the instrument Dinstat-Dis is 200 to 220 kg/cm². The sample weight decrease after residence in water for 28 days at the temperature of 37° C. is 20%. The composition is intended for fixation of electrodes, restoration of articular surfaces, fixation of bone homotransplantants in the case of anterior cervical spondyoledosis.

EXAMPLE 5

A composition for a temporary substitution of bone tissue defects consists of the following components, percent by weight:

| | |
|---|---|
| calcium carbonate | 30 |
| 1,4-di-N—oxy 2,3-diacetoxymethyl-quinoxaline | 10 |
| ethyl-α-cyanacrylate | 60. |

The composition is prepared in a manner similar to that of Examples 1 and 2. The cohesion strength of the cured conglomerate as determined on the instrument Dinstat-Dis (ultimate bending strength) is 250–280 kg/cm². The sample weight decrease after residence in water at the temperature of 37° C. for 28 days is 15%. The composition is intended for fixation of bone transplantants, filling of post-operation bone cavities with a volume of up to 2 cm³.

EXAMPLE 6

A composition for a temporary substitution of bone tissue defects consists of the following components, percent by weight:

| | |
|---|---|
| calcium gluconate | 30 |
| 4-uracylcarboxylic acid | 8 |
| kanamycin (antibiotic produced by Actinomyces kanamyceticus) | 12 |
| ethyl-α-cyanacrylate | 40 |
| ethoxyethyl-α-cyanacrylate | 10. |

The composition is prepared in a manner similar to that of Examples 1 and 2. The cohesion strength of the cured conglomerate determined on the instrument Dinstat-Dis (ultimate bending strength) is 200–220 kg/cm². The sample weight decrease after residence in water at the temperature of 37° C. for 28 days is 23%.

The composition is intended for filling post-operation bone cavities, fixation of bone fragments.

EXAMPLE 7

A composition for a temporary substitution of bone tissue defects consists of the following components, percent by weight:

| | |
|---|---|
| calcium gluconate | 30 |
| 1,4-di-N—oxy 2,3-dihydroxymethyl-quinoxaline | 12 |
| 4-uracylcarboxylic acid | 8 |
| ethyl-α-cyanacrylate | 48 |
| ethoxyethyl-α-cyanacrylate | 2. |

The composition is prepared in a manner similar to that described in Examples 1 and 2. The cohesion strength of the cured conglomerate as determined on the instrument Dinstat-Dis (ultimate bending strength) is 200 to 230 kg/cm². The sample weight decrease after residence in water at the temperature of 37° C. for 28 days is 25%.

The composition is intended for fixation of bone homotransplantants, filling of post-operation bone cavities in radical operations on patients suffering from chronical osteomyelitis and the like. The use of the composition in reconstruction stages of osteoplastic operations in otolaryngology has enabled a shortened duration of stay of the patients in the hospital by 4–6 days.

EXAMPLE 8 (COMPARATIVE)

A composition for a temporary substitution of bone tissue defects consists of the following components, percent by weight:

| | |
|---|---|
| modified bone chips | 50 |
| ethyl-α-cyanacrylate | 50. |

The cohesion strength of the composition determined on the instrument Dinstat-Dis (ultimate bending strength) is varied within the range of from 100 to 300 kg/cm². The sample weight loss after residence in water at the temperature of 37° C. for 28 days varies from 2 to 15% (at the constant proportions of the components).

What is claimed is:

1. A composition for a temporary substitution of bone tissue defects comprising α-cyanacrylic acid esters and a powder-like filler selected from the group consisting of a calcium salt of an organic acid and a calcium salt of an inorganic acid with a particle size of from 0.01 to 0.5 mm at the following proportions of the components, percent by weight:

| | |
|---|---|
| α-cyanacrylic acid esters | 60 to 40 |
| powder-like filler selected from the group consisting of calcium salt of an organic acid and calcium salt of inorganic acid with a particle size of from 0.01 to 0.5 mm | 40 to 60. |

2. A composition as claimed in claim 1, wherein as the calcium salt a salt is used selected from the group consisting of calcium gluconate and calcium carbonate.

3. A composition as claimed in claim 1, wherein a regeneration stimulant is additionally incorporated in an amount of from 10 to 30% by weight.

4. A composition as claimed in claim 3, wherein as the regeneration stimulant use is made of a compound selected from the group consisting of 4-uracylcarboxylic acid and derivatives thereof.

5. A composition as claimed in claim 1, wherein an antiseptic is additionally incorporated in an amount of from 10 to 30% by weight.

6. A composition as claimed in claim 5, wherein as the antiseptic use is made of 1,4-di-N-oxy 2,3-dihydroxymethylquinoxaline or 1,4-di-N-oxy 2,3-diacetoxymethylquinoxaline.

7. A composition as claimed in claim 1, wherein as the esters of α-cyanacrylic acid use is made of a mixture of ethyl-α-cyanacrylate and ethoxyethyl-α-cyanacrylate.

* * * * *